United States Patent [19]
van den Berg

[11] Patent Number: 5,184,505
[45] Date of Patent: Feb. 9, 1993

[54] METHOD AND DEVICE FOR DETERMINING THE QUALITY OF A SPECIFIC LUBRICANT FOR APPLICATION IN ROLLING BEARINGS OF A SPECIFIC TYPE

[75] Inventor: Antonie van den Berg, Montfoort, Netherlands

[73] Assignee: SKF Industrial Trading & Development Co. B.V., Nieuwegein, Netherlands

[21] Appl. No.: 706,228

[22] Filed: May 28, 1991

[30] Foreign Application Priority Data

Jun. 14, 1990 [NL] Netherlands .................. 9001353

[51] Int. Cl.$^5$ .................. G01N 33/30; G01N 29/02
[52] U.S. Cl. .................................. 73/53.05; 73/10
[58] Field of Search .............. 73/64, 10, 9, 593, 53.05, 73/64.53

[56] References Cited

U.S. PATENT DOCUMENTS

| | | | |
|---|---|---|---|
| 3,095,730 | 7/1963 | Matheson | 73/593 |
| 3,952,566 | 4/1976 | Jacobson | 73/10 |
| 4,007,630 | 2/1977 | Noda | |

FOREIGN PATENT DOCUMENTS

| | | | |
|---|---|---|---|
| 917059 | 3/1982 | U.S.S.R. | 73/64 |
| 1420454 | 8/1988 | U.S.S.R. | 73/10 |

OTHER PUBLICATIONS

J. F. Harris: 'The measurement of grease noise in electric motor grade ball bearings', Aug. 31, 1976, vol. 1A-12, No. 4, pp. 359-363.

M. W. Hauman: 'Acoustic emission monitoring of rolling element bearings', Oct. 5, 1988, Chicago, IL, pp. 885-889.

Patent Abstracts of Japan, vol. 8, No. 282 (P-323) (1719) Dec. 22, 1984 & JP-A-59 147 263 (Idemitsu Kosan K.K.) Aug. 23, 1984.

Primary Examiner—Hezron E. Williams
Assistant Examiner—Joseph W. Roskos
Attorney, Agent, or Firm—Rosen, Dainow & Jacobs

[57] ABSTRACT

Method for determining the extent to which noise occurs in a rotating roller bearing of a specific type lubricated with a specific lubricant, whereby an amount of the lubricant to be examined is applied to a roller bearing of the type mentioned, the inner race of the roller bearing is rotated for some time by means of a rotatable rod inserted in the inner race of the roller bearing until it interacts with it, and the vibrations occurring in the bearing are recorded by means of a vibration recorder which is in contact with the immobile outer race of the bearing, and a peak value is determined, following which these steps of the test cycle are repeated several times with new amounts of the same lubricant, characterized by the fact that a single roller bearing of the type specified is used in which every time, at the start of the steps of the test cycle, an amount of the lubricant to be tested is applied under pressure, whereby the amount of lubricant in the roller bearing which has been examined in a previous cycle is driven out under negative gas pressure before a new amount of lubricant is inserted into the bearing.

8 Claims, 2 Drawing Sheets

METHOD AND DEVICE FOR DETERMINING THE QUALITY OF A SPECIFIC LUBRICANT FOR APPLICATION IN ROLLING BEARINGS OF A SPECIFIC TYPE

The invention concerns in the first place determining the extent to which noise occurs in a rotating roller bearing of a specific type lubricated with a specific lubricant, whereby an amount of the lubricant to be examined is applied to a roller bearing of the type mentioned, the inner race of the roller bearing is rotated for some time by means of a rotatable rod inserted in the inner race of the roller bearing until it interacts with it, and the vibrations occurring in the bearing are recorded by means of a vibration recorder which is in contact with the immobile outer race of the bearing, and a peak value is determined, following which these steps of the test cycle are repeated several times with new amounts of the same lubricant.

It is very important for certain kinds of roller bearings that they be lubricated with a high-quality lubricant, i.e., a lubricant which, among other properties, has an excellent soap structure and contains little or no dust particles and/or crystals, which features reveal themselves due to the fact that they are typical noise generators in rotating roller bearings, so that it may be said that the less noise is being generated, the better the quality is of the lubricant involved.

It is therefore important to have a method with which the quality of various lubricants for application in specific roller bearings can be determined, so that it is possible to recommend that roller bearings of a specific type be lubricated with specific lubricants.

In the known method a number, e.g., ten, equal roller bearings are carefully cleaned and lubricated in the same manner with the lubricant to be examined, following which they are placed on the aforementioned rod and are rotated for a certain amount of time during which the aforementioned peak value is determined, so that ultimately ten peak values are obtained on the basis of which a statistic average can be calculated which is indicative of the quality of the lubricant. This method is very time-consuming and expensive.

The purpose of the invention is to find a method of the type described at the beginning, which involves less time and is cheaper.

The purpose is achieved due to the fact that in the method according to the invention a single roller bearing of the type specified is used in which every time, at the start of the steps of the test cycle, an amount of the lubricant to be tested is applied under pressure, whereby the amount of lubricant in the roller bearing which has been examined in a previous cycle is driven out under negative gas pressure before a new amount of lubricant is inserted into the bearing.

Accordingly, one needs only one roller bearing of a specific type, which remains connected to the rod for the entire period of examination, whereby the lubricant inside the bearing has to be replaced only a certain number of times, e.g., ten times, by a new amount. The latter can be done in a very simple way by inserting, every time, the amount of lubricant into the roller bearing by means of a plunger which moves linearly inside a tubular holder.

However, it has become clear that in following this method it is important, after the amount of lubricant has been inserted into the roller bearing by means of the plunger, to reverse the motion of the plunger because otherwise the peak values seem to be increasing as the measuring time progresses, so that they become unreliable. It appears that this phenomenon is the result of a reduced continuous supply of lubricant due to residual pressure in the lubricant after the plunger has come to a stop.

To remove any excess lubricant, the inner race is rotated for some time during the initial period, every time an amount of lubricant is being inserted into the bearing and before the measurements are made, following which any excess lubricant is removed from the bearing, preferably by means of compressed air.

The invention concerns also a device for applying the method, including a rod to be brought to rotation on which the inner race of a roller bearing can be placed until it interacts with it, and a vibration recorder which can be brought into contact with the outer race of the roller bearing whereby, according to the invention, a housing is placed around the roller bearing and the rod with a collector for the lubricant being driven from the bearing, which housing has furthermore a connection which is coupled to a device for bringing the lubricant into the housing under pressure, and a connection to a negative gas pressure source.

Preferably, the device for bringing lubricant into the housing under pressure includes a tube in which an amount of lubricant has been inserted, and a plunger which moves linearly back and forth inside the tube.

The invention will be explained further by means of the drawing in which.

Figure 1:
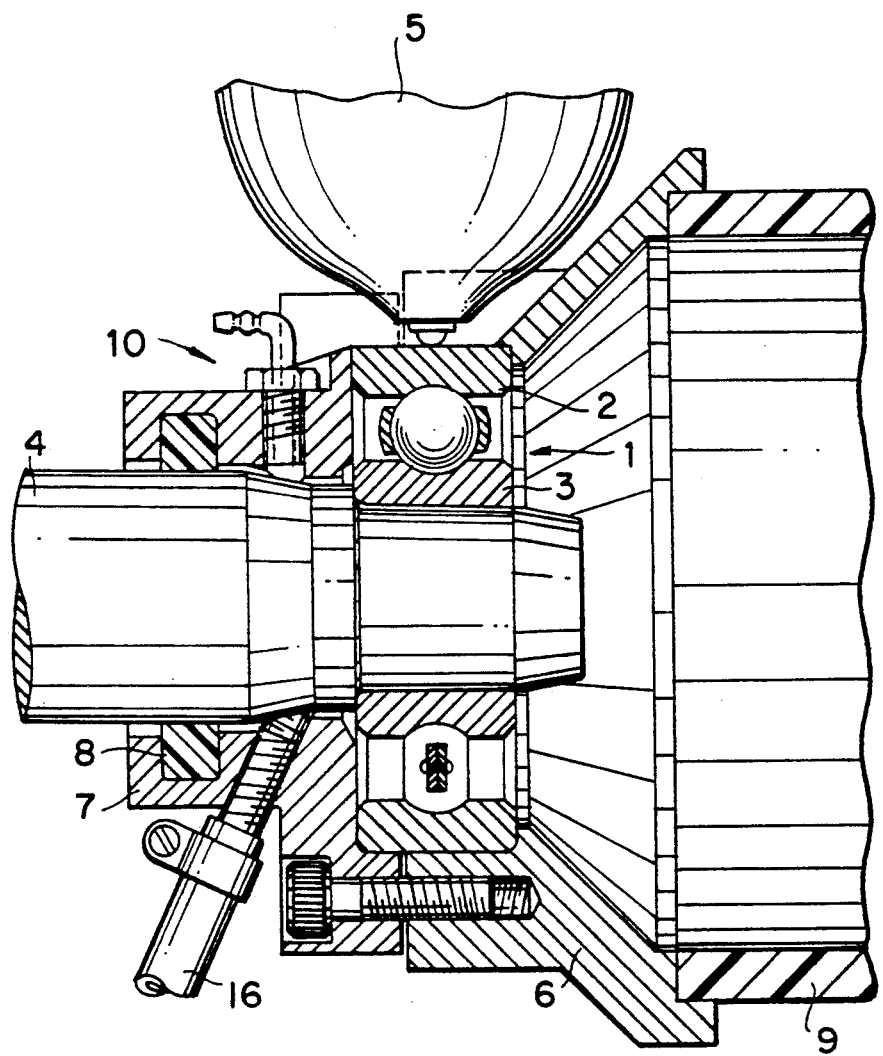
FIG. 1 shows an axial section of a device according to the invention.

As shown in FIG. 1, a roller bearing 1 with an outer race 2 and an inner race 3 is placed on a rod 4 which can be made to rotate, while a vibration recorder 5 is in contact with the outer race 2. The vibration recorder 5 is connected to a measuring device not shown here.

A housing has been placed around the bearing 1 and the rod 4 consisting of parts 6 and 7. Part 7 acts as a seal around rod 4 by means of a sealing ring 8, while part 6 is connected to a collector 9 for the lubricant being driven out.

Figure 2:
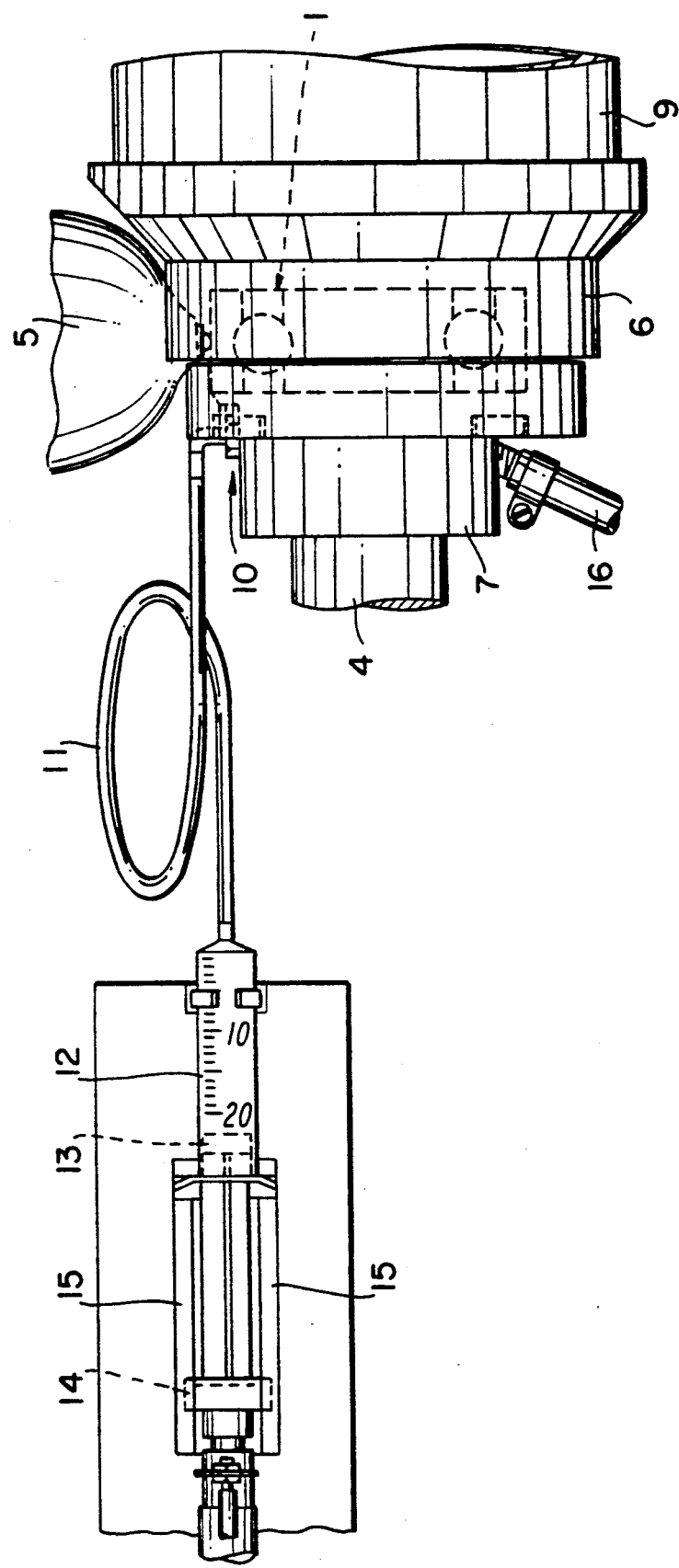
FIG. 2 shows the device for the insertion of lubricant coupled to the device according to FIG. 1.

The housing part 7 is equipped with a connection 10 which is linked by way of a hose 11 (see FIG. 2) to a tubular holder 12 which contains an amount of lubricant and in which a plunger 13 can move linearly back and forth in order to drive an amount of lubricant out of the tube 12 and into the bearing 1. In the embodiment shown, the tubular holder and the plunger 13 are parts of a syringe whereby the handle 14 of the plunger 13 is connected to a linearly moving mechanism and is led through pipes 15.

Furthermore, the housing part 7 is equipped with a connection 16 which is connected by way of a pipe—not shown here—to a negative gas pressure source—not shown either—e.g., compressed air.

To test a specific kind of lubricant, an amount of this lubricant is placed into the roller bearing 1 by means of a plunger 13 during, e.g., five seconds, after which the plunger motion is reversed for three seconds. Subsequently, the inner race 3 of the roller bearing is brought to rotation and, if needed, after an initial period of ten seconds, excess lubricant is blown out of bearing 1 during one second by means of compressed air supplied by way of the connection 16. Afterward, a peak value is measured each time after three seconds, until ten peak values have been obtained. Subsequently, the lubricant inside the bearing is removed entirely by means of the aforementioned compressed air, following which the steps described above are repeated ten times for the new amounts inserted in turn into the bearing 1, so that ultimately one hundred peak values are obtained for an accurate determination of the quality of the lubricant.

I claim:

1. A method for determining the quality of a lubricant used in roller bearing applications by measuring the extend to which noise occurs in the rotating roller bearing having an inner and outer race, said method comprising the steps of:
   (1) applying an amount of lubricant to a roller bearing;
   (2) rotating the inner race of a roller bearing using a rotatable rod inserted in the inner race of the roller bearing until the rod reacts with the bearing;
   (3) recording the vibrations occurring in the bearing using a vibration recorder in contact with the immobile outer race of the bearing and determining a peak value;
   (4) removing the lubricant entirely from the bearing using gas pressure,
   (5) repeating steps (1)-(4) several times.

2. The method of claim 1, wherein the step of applying lubricant to a roller bearing comprises the steps of moving a plunger linearly inside a tubular holder to drive lubricant out of a tube and into the roller bearing.

3. The method of claim 2, wherein the step of applying lubricant further comprises the step of moving the plunger in reverse after the lubricant has been inserted in the outer race of the bearing.

4. The method of claim 3 further comprising the step of removing excess lubricant from the bearing using compressed air after the inner race is rotated.

5. An apparatus for determining the extend to which noise occurs in a rotating roller bearing having a inner and outer race of a specific type lubricated with a specific lubricant, said apparatus comprising;
   means for applying an amount of lubricant to a roller bearing;
   means for rotating the inner race of a roller bearing by means of a rotatable rod inserted in the inner race of the roller bearing until the rod reacts with the bearing;
   means for recording the vibration occurring in the bearing, said recording means comprises a vibration recorder contacting the immobile outer race of the bearing and means for determining a peak valve.

6. The apparatus of claim 5 further comprising a housing positioned around the rolling bearing and the rod, said rod being connected to a collector for drawing out the lubricant.

7. The apparatus of claim 6, wherein said applying means applies the lubricant under pressure and further comprises a means for supplying gas pressure, said means for supplying gas being coupled to said housing.

8. The apparatus of claim 7, wherein said means for applying lubricant includes a tubular holder having lubricant inserted therein and a plunger than can move linearly back and forth inside the holder to insert the lubricant in the bearing.

* * * * *